United States Patent [19]
Watson

[11] Patent Number: 5,082,541
[45] Date of Patent: Jan. 21, 1992

[54] METHOD AND APPARATUS FOR CONTINUOUS ELECTROPHORESIS

[75] Inventor: Jack S. Watson, Knoxville, Tenn.

[73] Assignee: The United States of America as represented by the United States Department of Energy, Washington, D.C.

[21] Appl. No.: 551,387

[22] Filed: Jul. 10, 1990

[51] Int. Cl.$^5$ .................. B01D 57/02; B01D 61/42
[52] U.S. Cl. .................. 204/180.1; 204/299 R
[58] Field of Search .................. 204/299 R, 180.1

[56] References Cited

U.S. PATENT DOCUMENTS

| | | | |
|---|---|---|---|
| 3,616,453 | 10/1971 | Philpot | 204/299 |
| 3,844,926 | 10/1974 | Smyth et al. | 204/299 R |
| 3,989,613 | 11/1976 | Gritzner | 204/180 R |
| 4,061,560 | 12/1977 | Hannig et al. | 204/299 R |
| 4,148,703 | 4/1979 | Trop et al. | 204/180 G |
| 4,290,855 | 9/1981 | O'Farrell | 204/1.5 |
| 4,309,268 | 1/1982 | Richman | 204/180 R |
| 4,358,358 | 11/1982 | Rhodes | 204/299 R |
| 4,375,401 | 3/1983 | Catsimpoolas | 204/301 |
| 4,383,905 | 5/1983 | Richman | 204/180 R |
| 4,465,582 | 8/1984 | Richman | 204/299 R |
| 4,465,583 | 8/1984 | Lovegrove | 204/299 R |
| 4,473,452 | 9/1984 | Cantor et al. | 204/299 R |
| 4,617,103 | 10/1986 | Lovegrove | 204/300 R |
| 4,618,409 | 10/1986 | Lovegrove | 204/300 R |
| 4,642,169 | 2/1987 | Yoshisato et al. | 204/180.1 |
| 4,683,042 | 7/1987 | Scott | 204/180.1 |
| 4,732,656 | 5/1988 | Hurd | 204/182.4 |
| 4,752,372 | 6/1986 | Rhodes et al. | 204/299 R |

OTHER PUBLICATIONS

Vermeulen et al., "Design Theory and Separations in Preparative-Scale Continuous—Flow Annular—Bed Electrophoresis", Ind. Eng. Chem. Process Des. Develop., vol. 10, No. 1, 1971, pp. 91-102.

Mattock et al., "Velocity Gradient Stabilized, Continuous Free Flow Electrophoresis", A Review, Separation and Purification Methods, 9(1), 1-68, 1980, pp. 1-68.

Deyl, Z., "Electrophoresis, A Summary of Techniques and Applications", Elsevier Sci. Pub., New York, 1979, pp. 229-297.

Primary Examiner—John F. Niebling
Assistant Examiner—Cardine Koestner
Attorney, Agent, or Firm—David E. Breeden; Stephen D. Hamel; William R. Moser

[57] ABSTRACT

A method and apparatus for conducting continuous separation of substances by electrophoresis are disclosed. The process involves electrophoretic separation combined with couette flow in a thin volume defined by opposing surfaces. By alternating the polarity of the applied potential and producing reciprocating short rotations of at least one of the surfaces relative to the other, small increments of separation accumulate to cause substantial, useful segregation of electrophoretically separable components in a continuous flow system.

11 Claims, 4 Drawing Sheets

METHOD AND APPARATUS FOR CONTINUOUS ELECTROPHORESIS

The United States Governnment has rights in this invention pursuant to Contract No. DE-AC05-84OR21400 between the U.S. Department of Energy and Martin Marietta Energy Systems, Inc.

A METHOD AND APPARATUS FOR CONTINUOUS ELEGTROPHORESIS

BACKGROUND OF THE INVENTION

This invention relates generally to systems and methods for electrophoretic separati ly to improvements in continuous flow electrophoretic separation systems and methods.

Electrophoresis is a commonly used technique for separating minute quantities of small particles or macromolecules for analyses or characterization. Conventional approaches involve batch systems which are not capable of separating large or even significant quantities of the materials. To use electrophoresis for separating large quantities of materials to prepare useful and marketable quantities of separated materials, it is necessary to employ a means of continuous flow electrophoresis. Various systems and methods have been proposed to facilitate continuous electrophoresis separation in various flow-through systems of either a stationary free flow type or moving wall (usually continuous belts) type or single rotating cylindrical wall type. In each of these devices, a buffer, or carrier, liquid introduced at one end of a thin cross section chamber and drawn off at the other end to create a flowing curtain of liquid between a pair of electrodes of opposite polarity forming at least a portion of the confining walls of the chamber. By applying a voltage to the electrodes, an electric field is formed in the chamber transverse to the direction of flow in the chamber. A sample stream containing a mixture of various components capable of electrophoretic separation is injected into the buffer stream so that it flows through the chamber. As the sample is carried through the chamber, each component of the sample migrates toward the oppositely charged electrode a distance which is dependent upon the size of the component, the viscosity of the carrier liquid and the magnitude of the component charge. This causes like components of the sample to form into bands in the buffer stream across the width of the chamber between the electrodes. These separate bands of differing components are collected at the exit end of the chamber by means of zoned exit ports whose total flow is commensurate with the total flow of the sample and carrier.

Although various systems have been devised to compensate disruptive dynamic flow patterns in the chambers of flow-through systems due primarily to flow perturbations created from either containment wall frictional flow (Poiseuille flow) and/or electroosmosis due to the wall zeta potential, the known systems either add increasing complications to the design or operation of the flow system, making them ineffective for continuous flow production systems. These two flow disturbances combine in conventional electrophoretic separation devices to produce crescent-shaped flow distortion of the separated components in the otherwise laminar flow stream, making it difficult to collect the separated components at the different exit zones of the flow system. Accordingly, it will be appreciated that there is a need for an improved system and method of continuous flow electrophoresis.

SUMMARY OF THE INVENTION

In view of the above need, it is an object of this invention to provide an improved method and device for continuous flow electrophoretic separation which eliminates the flow perturbation problems associated with conventional electrophoresis separation methods.

Another object of this invention is to provide a method and device as in the above object in which more effective continuous separation is achieved through increased separation displacements of the components of the separated sample.

Briefly, the present invention is a method and device for continuously separating groups of particles with different electrophoretic mobilities in which improved separation is accomplished by the stepwise conversion of the small electrophoretic increments of separation into much larger increments by the alternate application of couette flow transverse to the direction of electrophoretic separation in a manner such that the larger increments of separation accumulate into substantial separations of the separable components as the components move through the system.

In accordance with one aspect of this invention, improved continuous flow electrophoretic separation of components of a sample material is accomplished by continuously introducing a carrier solution into an inlet end of a separator device for uniform laminar flow through a thin constant-width separation volume of the separator device wherein the volume is defined by a chamber having at least first and second wall portions uniformly spaced apart and disposed for controlled, reversible relative movement transverse to the direction of flow of the carrier solution through the separation volume, means for applying a uniform, reversible electric field to the volume in first and second directions transverse to the flow of the carrier solution and the direction of transverse movement of the walls of the chamber and a plurality of spaced apart collection ports at an outlet end of the chamber at positions along the extent of the chamber transverse to the width thereof commensurate with the corresponding zones of separated components of the sample stream carried by the carrier solution; continuously introducing the sample material having at least two electrophoretically separable components into the carrier stream at a central point between the walls of the chamber at the inlet end of the chamber; applying the electric field in the first direction for a period sufficient to produce differential increments of migration of the sample components in a first direction parallel to the direction of the applied electric field; moving one of the wall portions of the chamber relative to the other in a first direction to produce couette flow of the carrier solution and sample material in the separation volume sufficient to provide differential increments of separation of the electrophoretically separated components along a path parallel to the direction of movement of the one wall; applying the electric field in the second direction for a period sufficient to produce differential increments of migration of the sample components in a second direction parallel to the direction of the presently applied electric field; moving one of the wall portions of the chamber relative to the other in a second direction reverse to the first direction of wall movement to produce couette flow in the reverse direction sufficient to provide further differential increments of separation of the electrophoretically separated components along a path parallel to the direction of movement of the one wall; repeating the above reversible actions as the sample material traverses the separation volume; and collecting the separated constituents of the sample material along with the carrier solution at separate ones of the plurality of exit ports.

In accordance with a further aspect of this invention the device for carrying out the separation process may take the form of a cylindrical separation device wherein one wall of the separation chamber is a cylindrical stator and the other wall is a tubular rotor disposed to be reversibly rotated with respect to the stator, thereby defining an annular separation volume. Means are provided for applying a reversible electric field across the separation volume and rotating the rotor to effect separation of sample components introduced into a carrier medium filling the separation volume.

DETAILED DESCRIPTION OF PREFERRED EMBODIMENTS

Figure 1:
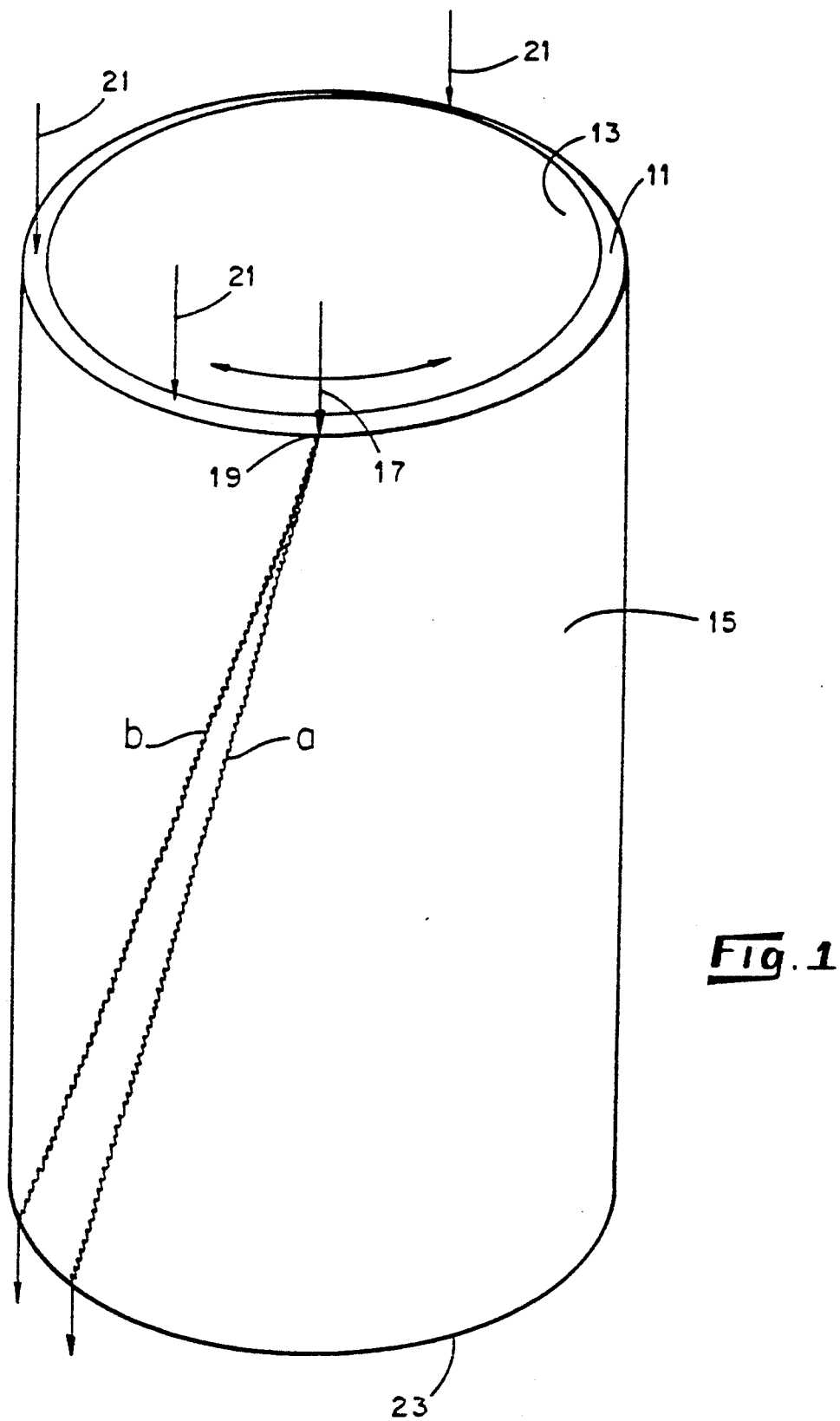
FIG. 1 is a schematic diagram of an annular separating volume illustrating the angular migration of two different weight particles a and b of a sample material to be separated introduced into a carrier solution flowing downward in the annulus.

Although it will be understood that the invention may be carried out in systems of either a cylindrical or planar geometry wherein the confining walls are flat plates disposed apart to form a planar separation volume and one plate is disposed to move relative to the other to produce the couette flow conditions, the invention will be described by means of illustrations of preferred cylindrical geometry embodiments. Referring now to FIG. 1, the continuous electrophoretic based separations take place within a thin annulus 11 confined by an inner surface 13 and an outer surface 15 which can be reversibly rotated relative to each other. The inner or outer surface, or both, may be rotated relative to each other first in one direction and then in the opposite direction. A continuous feed of mixed substances or particles 17 is injected into a point 19 in the up stream end of the annulus midway between the surfaces 13 and 15. A carrier solution 21 is introduced to fill and flow down the annulus. The thickness of the annulus 11 and rate of flow of the carrier solution is selected to provide laminar flow through the annulus. This prevents dispersion of the sample constituents and maximizes the separation efficiency. An electric field is applied uniformly across the annulus 11 which causes the particles to move by electrophoresis. Particles with different electrical charges, masses or shapes will move at different velocities, and the device is able to make the desired separation based upon these differences in electrophoretic velocities. The separated substances, such as the materials in zones a and b as shown for two substances, are separated as they flow through the system and may be collected as fractions at separate collecting locations angularly disposed about the annulus at the outlet end 23 of the annulus.

Figure 2:
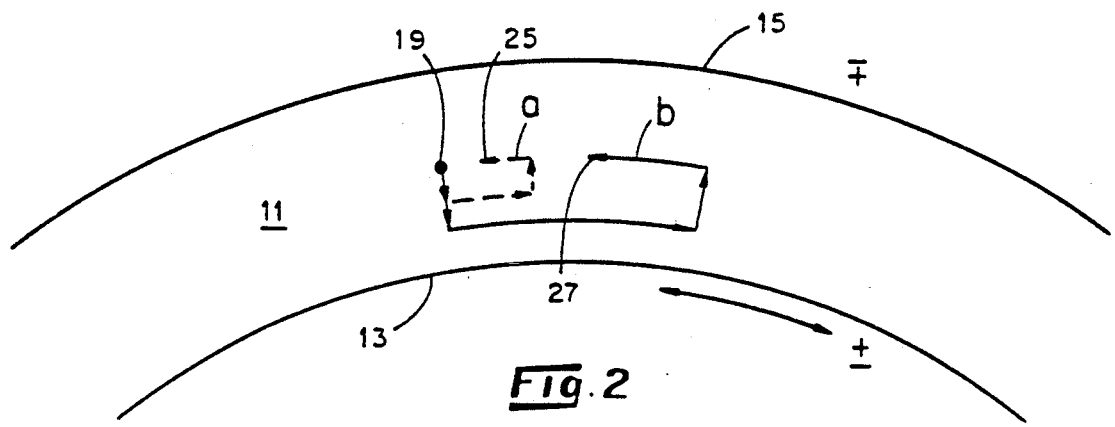
FIG. 2 is a schematic diagram of a portion of the annular separating volume illustrated in FIG. 1 illustrating the migration paths of the two different weight particles a and b from the annulus central introduction point 19.
Figure 3A:
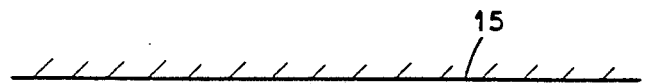
FIG. 3, which consists of FIGS. 3a and 3b, is a schematic diagram further illustrating the migration of particles with different electrophoretic mobility during one complete cycle of separative motion according to the method of the present invention.
Figure 3A:
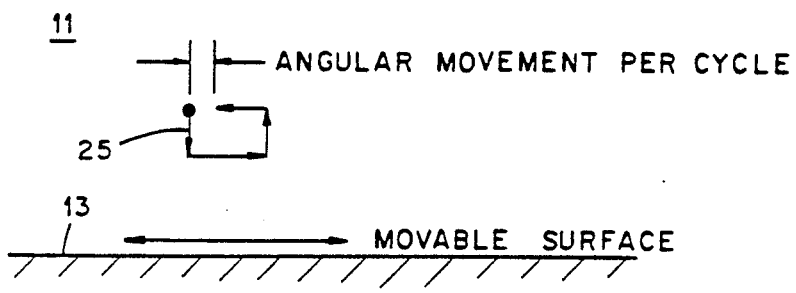

The trajectory of particles through the device depends upon the electrophoretic velocities. Although it is possible to have fluid motion while the electrophoresis is taking place, the most effective separation will occur with fluid motion and electrophoresis steps occurring separately as illustrated in FIG. 2. Particles enter at a center point 19 of the annulus 11. The particles are moved toward one wall of the annulus, depending on the direction of the applied electric field and the particle charge. In this case, both constituents migrate in the same direction, but one constituent (indicated by the broken line path 25) migrates slower than the other constituent (indicated by the solid line path 27). Then the electric field is turned "off" and the inner annular surface 13 is rotated clockwise. This action sets up a couette flow field between the two surfaces 13 and 15 wherein the velocity varies linearly across the annulus. Since the different particles have been displaced different distances normal to the surfaces 13 and 15 by the previous electrophoresis, the shear velocities will move the particles parallel to the annulus walls a distance proportional to their displacement by electrophoresis. Thus, the constituent migrating the slowest by electrophoresis will also be moved the shortest increment circumferentially by couette flow. As more clearly illustrated in FIG. 3, the movement of the less mobile particle along path 25, FIG. 3a, is much less than that of the movement of the more mobile particle along path 27, FIG. 3b, due to the difference in the initial radial movement produced by electrophoresis.

Figure 3B:
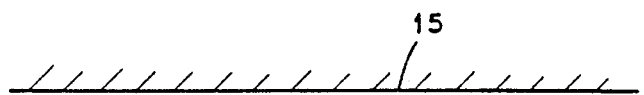
Figure 3B:
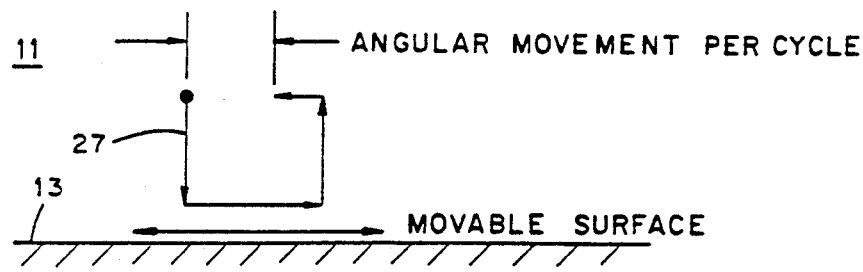

After a suitable rotation of the wall of the annulus (typically less than 15 degrees) to provide angular displacement of the particles, the rotation is stopped and the electric field polarity is reversed. This results in a migration of the particles back toward the center of the annulus. If the electric field is applied for the same period and at the same magnitude as the first application in the opposite direction, the particles will return to the same radial position in the annulus at which they were introduced but not in the same circumferential position. Then the annulus wall 13 is rotated in the opposite direction through the same angular displacement as the first rotation. However, the particles do not return to their initial circumferential location due to the difference in angular displacement during the couette flow condition produced in the annulus by the wall rotation. Thus, the resulting angular movement per cycle, as shown in FIGS. 3a and 3b, is different for each particle having a different electrophoretic mobility.

After the counter rotation of the annulus wall, the cycle is repeated continuously as the particles move down the annulus toward the exit end thereof. This means that the particles are continually migrating angularly in a stepwise fashion in the clockwise direction, as illustrated, with the more mobile particles moving more rapidly than the less mobile particles and oppositely charged particles going in the opposite direction. Other particles will be distributed angularly at appropriate positions between these limits. The downward flow of fluid sweeps the particles down the annulus so that each particle follows a trajectory defined by the lateral motion induced by the cumulative lateral electrophoretic movement combined with the subsequent couette flow effects and by the vertical motion induced by the downward flow of the carrier liquid. Thus, each particle will exit at the bottom of the annulus at an angular location depending upon its electrophoretic mobility.

Figure 4:
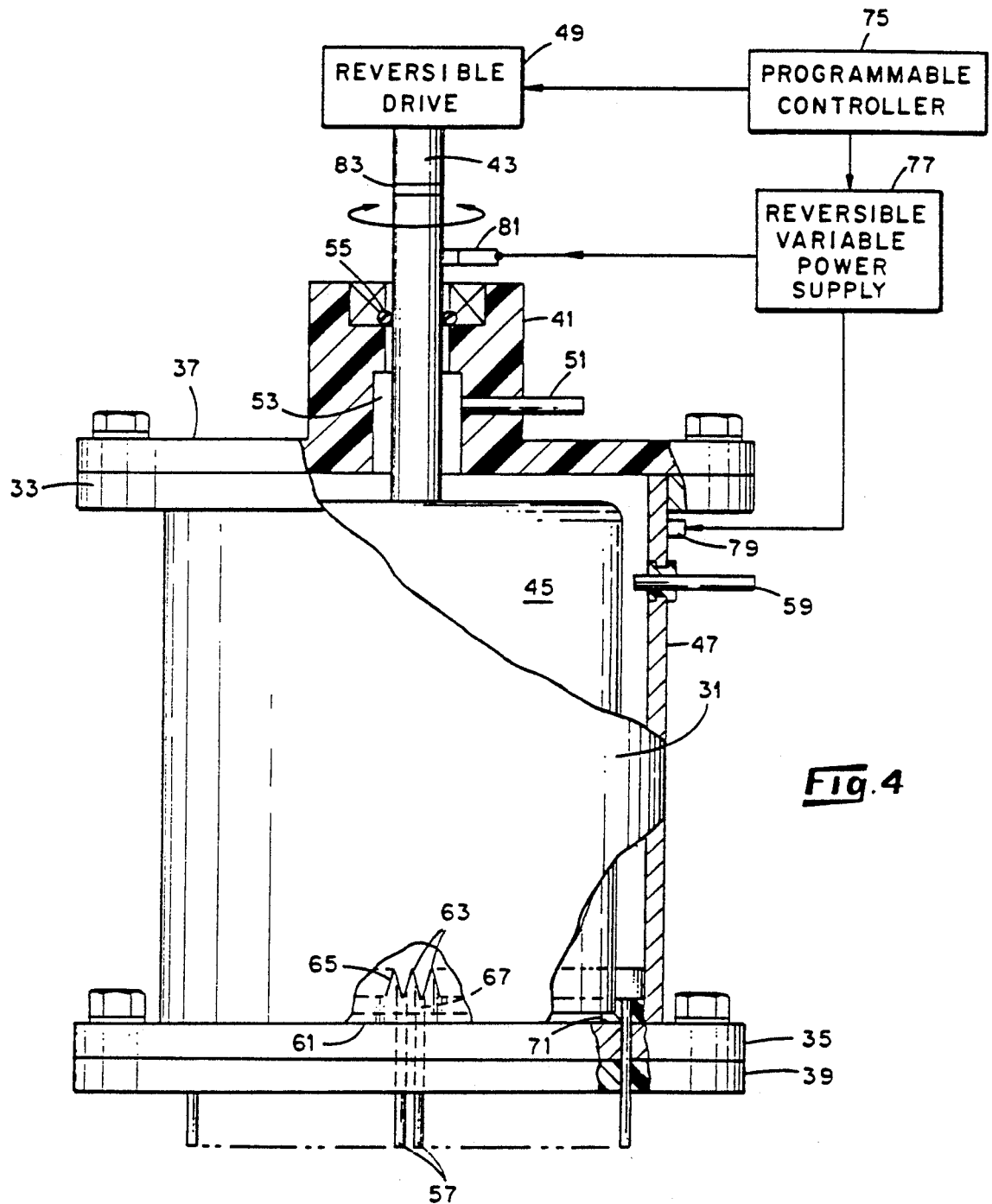
FIG. 4 is an elevation view, partially sectioned, of a cylindrical electrophoretic separation device made in accordance with the present invention having an annular separation volume as shown in FIG. 1.

Referring now to FIG. 4 a cylindrical continuous electrophoresis device is illustrated for carrying out the above method. The separator includes an outer stationary cylindrical housing 31 having top and bottom flanges 33 and 35 which are sealably attached to top and bottom end closure plates 37 and 39, respectively. The top end plate 37 is provided with a central hub portion 41 through which a shaft 43 extends which is attached to an inner cylindrical rotor 45. The rotor 45 is rotably disposed coaxially within the outer cylindrical wall 31 to form a uniform, thin cylindrical annulus 47 between the outer wall 41 and the inner cylinder 45 in which the separation action takes place. The inner and outer cylinders 31 and 45 are made of an electrically conductive material since they must also act as electrodes. The top and bottom plates, 37 and 39, may be constructed of a metal or a nonconductive material such as a structurally stable plastic. If the plates are formed of metal, the bolts, or other sealing means, must be electrically insulated so that the cylinders are electrically insulated from each other and unnecessary currents are not allowed to flow in the end plates 37 and 39 which may disrupt the separation process.

The inner cylinder 45 is rotated by a reversible drive 49 connected to the shaft 43. An inlet 51 for the carrier liquid is provided in the hub 41 which transports the particles to be separated down the annulus 47. The carrier liquid introduced through the inlet 51 flows into an annular chamber 53 disposed about the rotor shaft 43 which is sealed at the top by means of an O-ring seal 55. The carrier liquid flows through the volume formed by the spacing between the top of the rotor 45 and the end plate 37 which aids in distributing the flow to the annulus 47. For maximum symmetry in the carrier flow, additional inlets 51 may be located symmetrically about the hub 41.

The product mixture enters the device through a feed port inlet tube 59 in the side of the housing outer wall 41 near the top plate 33. The tube 59 extends into the annulus 47 to a the midpoint between the inner and outer walls of the annulus so that the product feed is introduced into the annulus carrier liquid flow at a central point in the annulus. Separation distances or circumferential positions at the exit end of the annulus are measured from the angular position of the feed inlet point. Since the spacing between the cylinder walls forming the annulus must be small, the positioning of the product feed inlet into the annulus must be precise in order for the system to work properly. For many separations it may be possible to use several inlet ports positioned at different locations about the annulus and connected for parallel flow to increase the separation capacity of the unit. Each inlet would be at the same axial position, but at different circumferential positions. It is only necessary to ensure that no two components from different inlet streams overlap and exit the device at the same circumferential position.

The bottom plate 39 contains a plurality of outlet tubes 57 located in a circle aligned with the annulus 47. To collect the separated products, circumferential collection zones are formed by means of a Teflon spacer ring 61 which may be attached to the lower plate 39 and disposed to extend a short distance into the lower end of the annulus 47. The upper side of the ring is machined to provide a series of sharp wedges 63 extending upward to form the boundaries of the collection zones. The downward flowing fluid falling within each collection zone is funneled into separate flow diverter grooves 65. Each of the grooves is provided with an outlet port 67 which is aligned with the corresponding outlet tube 57 extending through the lower plate 39 in fluid communication with the appropriate zone outlet port 67. The spacer ring could be constructed in one or several pieces; but in any form must provide the required electrical insulation between the inner and outer cylinder walls, as will be explained hereinbelow. The funneling arrangement of the spacer ring wedges 63 divert the flow while inhibiting circumferential remixing of the liquids during withdrawal and thus preserves the separation achieved in the annulus 47.

The separated product stream fractions together with the carrier liquid exit the annulus through the tubes 57. Due to the circumferential separation of the products in the annulus, different product fractions will exit at different tubes 57 about the annulus. The circumferential spacing of the outlet zones about the bottom of the annulus controls the resolution which can be achieved with this particular type of exit system. By using more and smaller collection zones, the resolution may be improved as desired.

As shown in FIG. 4, the spacer ring 61 may also be used to rotably support the rotor 45 within and in spaced relation with the outer cylinder 31 by means of a radially inward extending support ledge 71 upon which the lower end of the rotor rests for rotation thereon. The spacing between the rotor 45 and ring 61 is such that it provides a rotating low pressure seal to prevent leakage of the process fluids while allowing free rotation of the rotor relative to the spacer and outer cylinder 31.

The separation between the rotor 45 and the outer cylinder 31 surfaces forming the separation annulus 47 should be small enough to promote laminar flow in the annulus. Thus, it is necessary for the Reynolds number for flow in the annulus to be well below 2000, and preferably less than 1000. If water with a density of 1 g/cu cm and a viscosity of approximately 0.01 poise is used, the product of the velocity and the annulus spacing (expressed in units of cm/s and cm, respectively) should be considerably less than 20. Practical spacings for these conditions are on the order of about 2 to 5 mm. If necessary, the viscosity of the fluid may be increased by adding another material, such as glycerol, to the carrier and use larger spacings. The spacing in the drawings has been exaggerated in order to better illustrate the details of construction of the device.

To control the process, a programmable controller 75 is provided. The controller may take the form of a microprocessor which may be programmed to coordinate the rotation of the rotor 45 and the application of the selected potentials to the rotor 45 and housing surfaces 31 by generating and applying control signals to the reversible drive 49 and a reversible, variable power supply 77. The outputs of the power supply, whose polarities may be reversed in response to the control signal from the controller 75, are connected to the housing wall 31 at a terminal 79 connected thereto and to the rotor 45 by means of a brush 81 disposed to provide electrical contact with the rotor shaft 43. The shaft seal 45 must be formed of an electrically insulating material and the shaft is provided with an insulating section 83 above the point of contact of the brush 81 to electrically isolate the rotor from the drive 49.

In operation, once the required voltage for a separation process is determined, the potential is manually set in the power supply 77 and the polarity switching is controlled by the programmed controller 75. Prior to application of the sample materials to be separated to the inlet 59, the system is first filled with the appropriate carrier liquid. The outlet tubes for most applications will be small enough so that the device can hold the carrier liquid preload without draining. Capillary action will be sufficient to prevent liquid from seeping from the very small outlet tubes 57, as long as there is no vent near the top of the system. In embodiments requiring larger outlet tubes, it will be necessary to provide valves or clamps on the exit tubes 57 to prevent draining during the filling process. Alternatively, the device may be constructed so that the liquid flow through the system is upward, thereby eliminating the leakage problem. An upward flow embodiment will be described hereinbelow with reference to FIG. 5. Once the system is filled with a carrier liquid, the controller 75 is energized to control the process in accordance with that outlined above in the discussion with reference to FIGS. 13.

The pumping of the liquids into the system must be essentially free of perturbations so that no significant turbulence is introduced in the flow. A syringe pump is preferred for the sample feed stream since these pumps can handle small flow rates and will not shear biological materials which may be separated in the system. Either a gear or a syringe pump may be used for the carrier flow.

The reversible drive 49 must be smooth enough to prevent disturbances in the flow which could cause turbulence. A tightly coupled electric servo motor and gear or chain speed reduction system is preferred to avoid unnecessary jerking due to starting and stopping of the motor.

Figure 5:
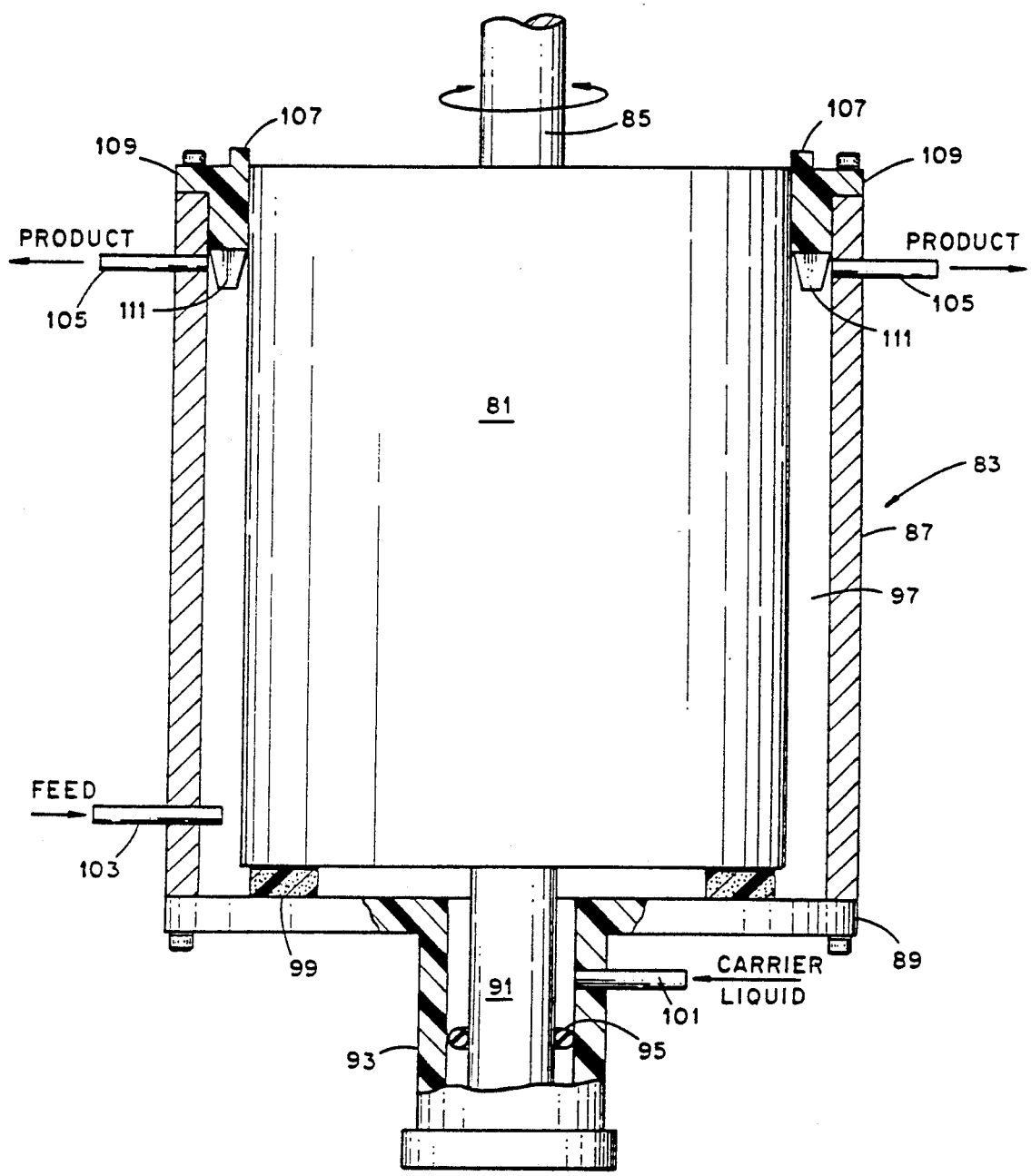
FIG. 5 is an elevation view, partially sectioned, of a cylindrical electrophoretic separation device made in accordance with the present invention in which the liquid flow is upward as opposed to the downward flow system shown in FIG. 4.

Referring now to FIG. 5, there is shown an alternate embodiment for upward flow of the process liquids. Like the embodiment shown in FIG. 4, the inner cylinder 81 is chosen to be the rotating surface and the outer surface formed by a cylindrical housing 83 is the stationary surface. The rotor 81 may be driven by means of a reversible drive, as shown in FIG. 4, connected to a shaft 85 of the rotor 81. The housing 83 is formed of an upright cylindrical portion 87 and a lower end cap 89 sealably attached to the wall portion 87. The end cap has a central hub portion 93 adapted to rotatably receive a lower end shaft 91 of the rotor 81 by means of an O-ring seal 95. The seal 95 provides alignment of the rotor relative to the housing wall 87 as well as a seal for the process liquid flow in the annulus. The housing wall 87 and the rotor 81 are constructed of an electrically conductive material and forms the electrodes of the device which may be connected as illustrated in FIG. 4. The end cap 89 may be formed of a stable plastic material to provide electrical insulation between the rotor 81 and the housing wall 87. The end cap 89 may be bolted to a flange on the wall portion to form a sealed connection. The spacing between the rotor 81 and the cylinder 87 forms the separation annulus 97 through which the process liquids flow in an upward direction.

The weight of the rotor may be supported by either a bearing in the hub 93 which engages the end of the shaft 91 or by means of an annular porous ring support member 99 which also provides the needed flow resistance to promote uniform flow of the carrier liquid into the separation annulus 97. This support may be constructed of a porous Teflon ring having a smooth upper bearing surface for low resistance sliding engagement with the bottom surface of the rotor 81. The carrier liquid flow is introduced into the annular chamber formed between the rotor shaft 91 and the housing hub 93 through an inlet port 101 and flows upward through the annulus 97. The sample feed is introduced into the carrier liquid through a feed port 103 located in the housing wall 87. The separated sample materials together with the carrier liquid exit the annulus through a plurality of exit ports 105 distributed about the top of the housing wall 87. A spacer/flow diverter ring 107 is provided at the top of the annulus which extends into the annulus in sliding contact with the rotor 81. The ring is mounted by means of bolting a flange portion 109 thereof to the upper edge of the housing wall portion 87 so as to provide precise spacing between the rotor 81 and the outer wall 87 at the top of the annulus. The ring 107 is provided with downward extending wedge portions 111 which protrude down into the annulus to form individual flow channels for the corresponding exit ports 105, similar to that shown in FIG. 4 with the exception that the flow exits the outer side rather than through the base of the diverter channel. In this embodiment, a sealing surface over the top of the device is not required.

Although the invention has been described through illustrations of embodiments to separate a large number of different particles according to their electrophoretic mobility, the concept of combined electrophoretic and couette flow may be applied without the vertical, or carrier, flow when only binary mixtures having two particles with opposite charge are to be separated. The vertical motion would be ignored and the two particles of the mixture would simply migrate under the alternating electrophoretic and hydrodynamic fields in opposite directions about the annulus from the feed point. The feed and product withdrawal locations would not then have to be at a single point but could be along lines parallel to the axis of the annulus.

If the two particles to be separated are of like charge, the vertical flow could be replaced with a circumferential flow in the direction opposite of the travel produced by the electrophoretic and couette flow. When properly adjusted, this flow would sweep the more slowly moving particles back past the inlet and allow the more rapidly moving particles to proceed against the circumferential flow. Under these conditions, the feed and product withdrawal could be along vertical lines.

Thus, it will be seen that an improved method of continuous electrophoresis together with versatile apparatus for carrying out the method have been provided. Although the invention has been illustrated by means of descriptions of specific embodiments thereof, it will be understood by those skilled in the art that various modifications and changes may be made therein without departing from the spirit and scope of the invention as set forth in the following claims attached to and forming a part of this specification.

What is claimed is:

1. A method for continuous electrophoretic separation of components of a sample material having different electrophoretic mobilities, comprising the steps of:
   a. introducing a carrier solution into a thin constant-width separation volume of a separator device wherein the volume is defined by a chamber having at least first and second wall portions uniformly spaced apart and disposed for controlled, reversible relative movement, means for applying a uniform, reversible electric field to the volume in first and second directions transverse to the direction of movement of said wall portions of the chamber and a plurality of spaced apart collection ports at positions along said chamber commensurate with the corresponding zones of separated components of said sample;
   b. introducing said sample material having at least two electrophoretically separable components into said carrier at a point between the walls of the chamber at an inlet of said chamber;
   applying said electric field in said first direction for a period sufficient to produce differential increments of migration of the sample components in a first direction parallel to the direction of the applied electric field;
   d. moving one of said wall portions of said chamber relative to the other in a first direction to produce couette flow of the carrier solution and sample material in the separation volume sufficient to provide differential increments of separation of the electrophoretically separated components along a path parallel to the direction of movement of the said one wall portion;
   e. applying said electric field in said second direction for a period sufficient to produce differential increments of migration of said sample components in a second direction parallel to the direction of the presently applied electric field;
   f. moving said one wall portion of said chamber relative to the other in a second direction reverse to the first direction of wall movement to produce couette flow in the reverse direction sufficient to provide further differential increments of separation of the electrophoretically separated components along a path parallel to the direction of movement of the said one wall;
   g. repeating steps c through f to produce a net separation of said components of said sample in directions parallel to said wall portions; and
   h. collecting the separated components of the sample material.

2. A method for continuous electrophoretic separation of components of a sample material having different electrophoretic mobilities, comprising the steps of:
   a. continuously introducing a carrier solution into an inlet end of a separation volume of a separator device wherein the volume is defined by a chamber having at least first and second wall portions uniformly spaced apart and disposed for controlled, reversible relative movement transverse to the direction of flow of the carrier solution through the separation volume, means for applying a uniform, reversible electric field to the volume in first and second directions transverse to the flow of the carrier solution and the direction of transverse movement of said wall portions of the chamber and a plurality of spaced apart collection ports at an outlet end of the chamber at positions along the extent of the said chamber transverse to the width thereof commensurate with the corresponding zones of separated components of said sample stream carried by the carrier solution;
   b. continuously introducing said sample material having at least two electrophoretically separable components into said carrier stream at a point between the walls of the chamber at said inlet end of said chamber;
   c. applying said electric field in said first direction for a period sufficient to produce differential increments of migration of the sample components in a first direction parallel to the direction of the applied electric field;
   d. moving one of said wall portions of said chamber relative to the other in a first direction to produce couette flow of the carrier solution and sample material in the separation volume sufficient to provide differential increments of separation of the electrophoretically separated components along a path parallel to the direction of movement of the said one wall portion;
   e. applying said electric field in said second direction for a period sufficient to produce differential increments of migration of said sample components in a second direction parallel to the direction of the presently applied electric field;
   f. moving said one wall portion of said chamber relative to the other in a second direction reverse to the first direction of wall movement to produce couette flow in the reverse direction sufficient to provide further differential increments of separation of the electrophoretically separated components along a path parallel to the direction of movement of the said one wall;
   g. repeating the above reversible actions as the sample material traverses the separation volume; and
   h. collecting the separated components of the sample material along with the carrier solution at separate ones of said plurality of exit ports.

3. The method as set forth in claim 2 wherein said first and second wall portions are cylindrical wall portions.

4. The method as set forth in claim 3 wherein said separation volume is a thin constant-width separation annulus and the carrier solution is introduced into said annulus in a manner to produce uniform laminar flow through said annulus.

5. The method as set forth in claim 4 wherein said sample material is introduced into said separation annulus at a point midway between said first and second wall portions.

6. A continuous flow electrophoretic separator, comprising:
   a separation chamber having a stationary wall portion and a reversibly movable wall portion disposed in parallel spaced relation to said stationary wall portion to form an electrophoretic separation volume between said wall portions and movable relative thereto along a selected path parallel to said stationary wall;
   means for introducing a carrier liquid into said volume;
   means for continuously receiving a sample material having at least two components of different electrophoretic mobilities to be separated into said separation volume at a position between said wall portions at an inlet end of said separation volume;

a plurality of outlet ports connected in fluid communication with said separation volume at an outlet end thereof and located for receiving corresponding components of said sample material; for controllably applying a reversible electric power supply means field uniformly across said separation volume perpendicular to said wall portions to effect electrophoretic separation of said components of said sample material along lines parallel to said electric field;

moving said movable wall reversible drive means for controllably moving said movable wall portion sufficient to produce reversible couette flow of said carrier liquid in said separation volume; and a control means for controlling said power supply and said drive means to alternate the polarity of said electric field with the reversible movement of said movable wall by said drive means to effect an accumulative separation of said electrophoretically separable components of said sample as they migrate through said separation volume in said carrier liquid from said inlet end to said outlet end under the combined influence of said reversible electric field and reversible couette flow.

7. The separator as set forth in claim 6 wherein said chamber is a cylindrical chamber having a cylindrical stator forming said stationary wall portion and a rotor forming said movable wall portion separated sufficiently to form a separation annulus therebetween.

8. The separator as set forth in claim 7 wherein said rotor and said stator are formed of an electrically conductive material and further includes means for electrically insulating said rotor from said stator and means for electrically connecting said rotor and said stator to separate reversible output of said power supply so that said rotor and said stator act as electrodes for providing said reversible electric field across said separation annulus.

9. The separator as set forth in claim 8 wherein said means for introducing a carrier liquid into said separation volume includes means for continuously introducing said carrier liquid into said separation annulus uniformly about the inlet end of said cylindrical chamber and collecting said carrier liquid with said separate sample components at said exit end of said chamber.

10. The separator as set forth in claim 9 further comprising a flow diverting means located in said separation annulus at said outlet end thereof for collecting and diverting said separated components of said sample material into said plurality of outlet ports, said diverter means being formed of an electrically insulating material and forming a spacing ring for spacing said rotor from said stator at said outlet end.

11. The separator as set forth in claim 10 wherein said means for introducing said sample material into said separation annulus includes an inlet tube disposed to dispense said sample material into said carrier liquid at a point midway between said wall portions.

* * * * *